(12) United States Patent
Kanematsu (10) Patent No.: US 6,385,288 B1
(45) Date of Patent: May 7, 2002

(54) RADIOTHERAPY APPARATUS WITH INDEPENDENT ROTATION MECHANISMS

(75) Inventor: Nobuyuki Kanematsu, Tokyo (JP)

(73) Assignee: Mitsubishi Denki Kabushiki Kaisha, Tokyo (JP)

(*) Notice: Subject to any disclaimer, the term of this patent is extended or adjusted under 35 U.S.C. 154(b) by 0 days.

(21) Appl. No.: 09/870,796

(22) Filed: Jun. 1, 2001

(30) Foreign Application Priority Data

Jan. 19, 2001 (JP) ........................................ 2001-012284

(51) Int. Cl.[7] ................................................ A61N 5/10
(52) U.S. Cl. ............................................. 378/65; 378/9
(58) Field of Search ................................ 378/4, 9, 65

(56) References Cited

U.S. PATENT DOCUMENTS 4,998,268 A * 3/1991 Winter ........................ 378/63
5,117,829 A * 6/1992 Miller et al. .............. 128/653.1
5,291,404 A    3/1994 Kurokawa et al.
5,317,164 A    5/1994 Kurokawa
5,548,627 A    8/1996 Swerdloff et al.
5,596,653 A    1/1997 Kurokawa

FOREIGN PATENT DOCUMENTS

JP    59-76    1/1984

* cited by examiner

Primary Examiner—David P. Porta
Assistant Examiner—Elizabeth Gemmell
(74) Attorney, Agent, or Firm—Oblon, Spivak, McClelland, Maier & Neustadt, P.C.

(57) ABSTRACT

A novel radiotherapy apparatus is disclosed, comprising: a bed; an X-ray source for CT; an X-ray detector for CT; a CT rotating mechanism for supporting the CT X-ray source and the CT X-ray detector rotatably around the bed; a radioactive ray source for therapy; a collimator; and a therapy rotating mechanism for supporting the radioactive ray source and the collimator rotatably around the bed independently of the CT rotating mechanism.

7 Claims, 3 Drawing Sheets

ically, the invention is directed to a radiotherapy

RADIOTHERAPY APPARATUS WITH INDEPENDENT ROTATION MECHANISMS

BACKGROUND OF THE INVENTION

1. Field of the Invention

The present invention relates to a radiotherapy apparatus. More particularly, the invention is directed to a radiotherapy apparatus, which can be controlled based on a radiotherapy plan made by referring to a CT image obtained from an integrally provided CT device.

2. Description of the Related Art

With regard to currently practiced radiotherapy, a treatment is generally carried out by operating the CT device, a therapy planning device, a patient positioning device including a bed, and a radioactive ray irradiating device in linkage. Specifically, the CT device is used to form a CT image regarding the affected part of a patient by picking up the image thereof; the therapy planning device to create setting information for each device involved in radioactive ray irradiation according to each case by referring to a three-dimensional image obtained from the CT device; and the radioactive ray irradiating device to treat a disease, such as a tumor or the like, present in the body of the patient by irradiating a diseased part with radioactive rays, e.g., X-rays or electron beams. Usually, the combination of the patient positioning device and the radioactive ray irradiating device is referred to as a radiotherapy apparatus.

Conventionally, the CT device and the radioactive ray irradiating device have been installed in places away from each other, and separately operated. However, for the purpose of enhancing operability and therapy performance by increasing linkage among the devices involved in radiotherapy, and reducing overall costs, requests have been made to integrate such devices. To meet these demands, efforts have been made to develop an apparatus, which includes, for example, a linear acceleration CT disclosed in Japanese Patent Application Laid-Open No. 1984-000076, and a tomographic therapy device disclosed in U.S. Pat. No. 5548627.

Figure 6:
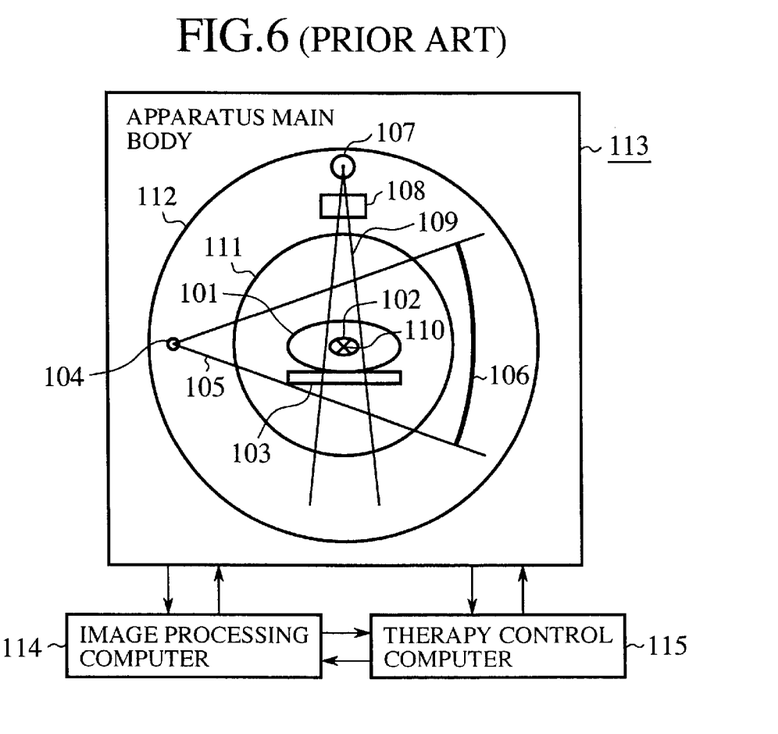
FIG. 6 is a schematic sectional view showing a constitution of a conventional tomographic therapy device.

FIG. 6 is a schematic sectional view of the constitution of the above-noted tomographic therapy device, specifically showing a case where the portion of a device main body is seen from the foot or head side of a patient. In FIG. 6, a reference numeral 10.1 denotes a patient to be treated; 102 an affected part of the patient 101; 103 a bed for the patient 101; 104 an X-ray source for CT; 105 an X-ray beam for CT, radiating from the CT X-ray source 104; 106 an X-ray detector for CT; 107 a radioactive ray source for therapy; 108 a collimator; and 109 a radiation beam for therapy, radiating from the therapy radioactive ray source 107. The CT X-ray source 104, the CT X-ray detector 106, the therapy radioactive ray source 107 and the collimator 108 are mounted on the same endless rotating mechanism. A reference numeral 110 denotes a geometrical center axis. The CT X-ray source 104 and the therapy radioactive ray source 107 are secured to the endless rotating mechanism in such a way as to be separated from each other by 90° seen from the center axis 110. A reference numeral 111 denotes an inner wall portion inhibited from being rotated; 112 an outer wall portion similarly inhibited from being rotated; and 113 a device main body including the bed 103, the CT X-ray source 104, the CT X-ray detector 106, the therapy radioactive ray source 107, the collimator 108, the inner and outer wall portions 111 and 112, and other members, not shown. A reference numeral 114 denotes an image processing computer for forming a CT image regarding an affected part or the like, and creating control information regarding the device main body 113 by referring to the CT image; and 115 a therapy control computer for controlling each device involved in the execution of radiotherapy based on the control information. Interconnections are made between the computers, and between the computers and the above devices by a not-shown network, and information is transferred around by an analog or digital signal.

Now, the typical structures of a radiotherapy apparatus and a CT device developed and made available in the conventional art are described. The radiotherapy apparatus is constructed in such a manner that a gantry head as a beam radiation portion is provided in a gantry installed as an arm-shaped supporting frame, and this gantry is mounted on a rotating mechanism provided in a device main body fixed in a therapy room. The CT device is constructed in such a manner that inside a cylindrical image pickup device, into which a bed carrying a patient can be inserted, an X-ray tube and an X-ray detector are provided symmetrically to the center axis of the cylindrical body, and a rotating mechanism is provided in a device main body for rotating the cylindrical body around the patient. The X-ray detector provided in the CT device comprises a row of detecting elements disposed in an arc shape, and can pick up the image of one section by one rotation. The parallel arrangement of such a plurality of detecting elements also enables multi-slicing to be realized, which simultaneously picks up a plurality of sections by one rotation.

Next, the operation of the tomographic therapy device shown in FIG. 6 is described.

After the patient 101 is secured to the bed 103, X-rays radiate from the CT X-ray source 104 while the endless rotating mechanism is rotated. Then, by using the CT X-ray detector 106 to detect the X-rays passed through the patient 101, image pickup data is obtained regarding one section of the affected part of the patient 101. The image processing computer 114 receives a signal regarding the image pickup data outputted from the CT X-ray detector 106, and forms a CT image of the affected part for each rotation of the endless rotating mechanism. When necessary, this process is repeated to form a three-dimensional image. Then, based on the formed CT image, the image processing computer 114 creates control information to generate a therapy radiation beam 109 necessary for realizing proper radiotherapy. In the described tomographic therapy device, the therapy radiation beam 109 is generated while the endless rotating mechanism is rotated as in the case of CT photographing. Accordingly, control information is created in such a way as to optimize setting regarding the opening state or the like of the collimator 108 for each position on a rotational path of the therapy radioactive ray source 107.

The control information thus created is then sent as therapy plan information to the therapy control computer 115. Based on the provided therapy plan, and according to the rotation of the endless rotating mechanism, the therapy control computer 115 executes radiotherapy by converging radioactive rays radiating from the therapy radioactive ray source 107, by the collimator 108, to match the shape of the patient 101. When the endless rotating mechanism disposed between these wall portions or each device mounted on the endless rotating mechanism is rotated, the presence of the inner and outer wall portions 111 and 112 can prevent the clashing of such a rotating object with the patient 101, the bed 103 or other external objects.

However, some problems have been inherent in the foregoing constitution of the tomographic therapy device made available as the radiotherapy apparatus in the conventional art. Specifically, the integrated arrangement of the CT device and the radioactive ray irradiating device on the same endless rotating mechanism has resulted in the increases in weight and volume of the rotating mechanism, creating the mechanical difficulty of achieving high-speed rotation necessary for the CT device.

To rotate the radioactive ray irradiating device at a high speed as in the case of the CT device, it is essential to achieve high-speed control at the radioactive irradiating device side. Particularly in the case of the collimator for mechanically controlling a field of irradiation, there has been a difficulty of changing each setting at a high speed according to a rotational angle.

Furthermore, since the therapy radioactive ray source generally uses a large-output high frequency, the mounting thereof with the CT device on the same endless rotating mechanism itself has been technically difficult.

SUMMARY OF THE INVENTION

The present invention has been made to solve the foregoing problems, and it is an object of the invention to provide a radiotherapy apparatus comprising a radioactive ray irradiating device and a CT device provided in one device, and capable of guaranteeing desired operational characteristics required of the radioactive ray irradiating device and the CT device.

A radiotherapy apparatus provided by the invention comprises: a bed, a position thereof being adjustable; an X-ray source for CT; an X-ray detector for CT; a CT rotating mechanism for supporting the CT X-ray source and the CT X-ray detector rotatably around the bed; a radioactive ray source for irradiating radioactive rays for therapy; a collimator provided for converging a shape of a therapy radiation beam radiating from the radioactive ray source; and a therapy rotating mechanism for supporting the radioactive ray source and the collimator rotatably around the bed independently of the CT rotating mechanism.

The radiotherapy apparatus of the invention further comprises: correction amount computing means for computing deviation in a position or a direction of an affected part by comparing a CT image obtained by photographing carried out by using a CT device composed of a CT X-ray source and a CT X-ray detector, and referred to when a therapy plan is made, with a CT image obtained by photographing carried out by using the CT device immediately before radiotherapy.

The radiotherapy apparatus of the invention further comprises: radioactive ray irradiation control means for performing control to detect a relative angle difference between the therapy rotating mechanism and the CT rotating mechanism, and stop irradiation of radioactive rays from the radioactive ray source in a range of angles, interference occurring in therapy radioactive rays therein.

In the radiotherapy apparatus of the invention, affected part information recording means is provided for recording time and space information regarding an affected part currently subjected to radiotherapy, obtained by executing CT photographing simultaneously with the radiotherapy.

The radiotherapy apparatus of the invention further comprises: image processing means for forming a CT image regarding an affected part or the like, and transmitting data of the CT image through a network; and therapy control means for receiving an entry of therapy plan information through the network, and controlling each device involved in execution of radiotherapy based on the therapy plan information.

The radiotherapy apparatus of the invention further comprises: affected part position detecting means for detecting an affected part position in real time.

The radiotherapy apparatus of the invention further comprises: affected part shape detecting means for detecting an affected part shape in real time.

DESCRIPTION OF THE PREFERRED EMBODIMENTS

Next, the preferred embodiments of the present invention will be described with reference to the accompanying drawings.

First Embodiment

Figure 1:
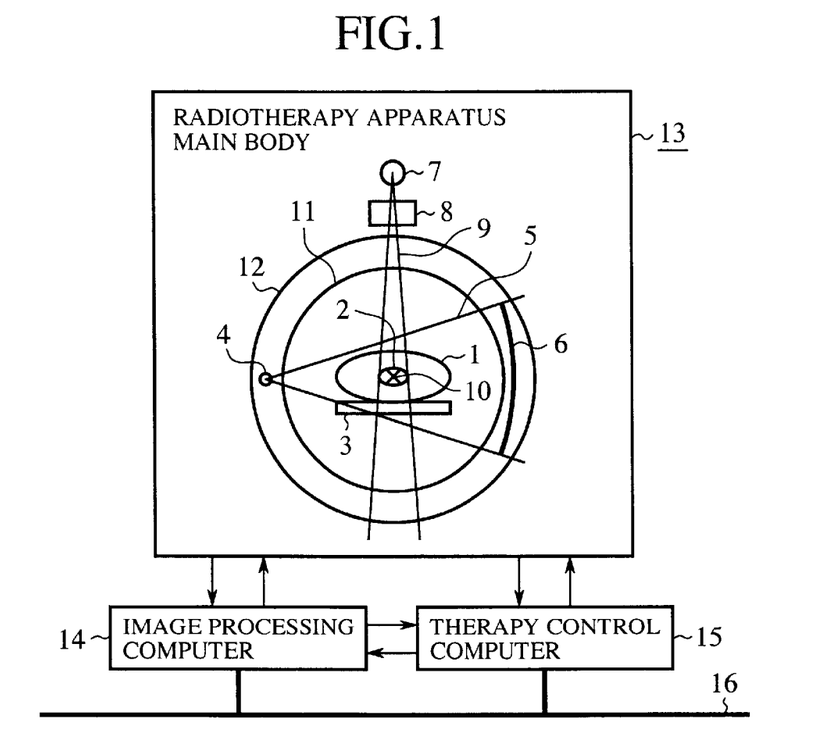
FIG. 1 is a schematic sectional view showing a constitution of a radiotherapy apparatus according to a first embodiment of the present invention.

FIG. 1 is a schematic sectional view of the constitution of a radiotherapy apparatus according to the first embodiment of the invention. This sectional view specifically shows a case where the portion of an apparatus main body is seen from the foot or head side of a patient. In FIG. 1, a reference numeral 1 denotes a patient to be treated; 2 an affected part of the patient 1; 3 a bed for securing the patient 1, equipped with a position adjusting mechanism for positioning the patient 1; 4 an X-ray source for CT; 5 an X-ray beam for CT, radiating from the CT X-ray source 4; 6 an X-ray detector for CT; 7 a radioactive ray source for therapy; 8 a collimator; and 9 a radiation beam for therapy, irradiated from the therapy radioactive ray source, the beam shape thereof being converged by the collimator 8. The CT X-ray source 4 and the CT X-ray detector 6 are installed in a CT rotating mechanism. The therapy radioactive ray source 7 and the collimator 8 are installed in a therapy rotating mechanism. A reference numeral 10 denotes a geometrical center axis for the CT and therapy rotating mechanisms; 11 a cylindrical inner wall portion; 12 a cylindrical outer wall portion; and 13 a radiotherapy apparatus main body composed of the bed 3, the CT X-ray source 4, the CT X-ray detector 6, the therapy radioactive ray source 7, the collimator 8, the inner and outer wall portions 11 and 12, and other not-shown members. The CT and therapy rotating mechanisms are mounted on the apparatus main body 13 so as to be rotated independently of each other.

With regard to the radiotherapy apparatus including the CT and therapy rotating mechanisms to be rotated independently of each other as described above, various structures can be employed for its realization by using existing technologies like those noted-above in the related art. For example, for the therapy rotating mechanism, the rotating mechanism of the conventional radiotherapy apparatus can be used without any changes. On this assumption, for a cylindrical CT device, a cantilever supporting structure may be employed to secure it to a fulcrum portion fixed in a therapy room or to a gantry mounted on the fulcrum portion. In the case of fixation to the gantry, the CT device should preferably be attached to the gantry in such a way as to set the rotational axis of the gantry and the center axis of a cylindrical body provided as the CT device coaxial to each other. In this state, it is possible to obtain desired operational characteristics by rotating the CT X-ray source 4 and the CT X-ray detector 6 between the cylindrical inner and outer wall portions 11 and 12, independently of each other with respect to both wall portions.

More specifically, the radiotherapy apparatus may be constructed in such a manner that the CT X-ray source 4 and the CT X-ray detector 6 are supported on a gantry smaller than that for supporting the radioactive ray irradiating device, and the small gantry is mounted on another high-speed endless rotating mechanism having a center axis set coaxial to that of the rotating mechanism of the gantry for supporting the radioactive ray irradiating device. In this case, the inner and outer wall portions 11 and 12 for protecting a patient or the like from the high-speed rotation of the CT device may be secured to the gantry for supporting the radioactive ray irradiating device. Thus, by providing a double gantry composed of a gantry for supporting the radioactive ray irradiating device and a gantry for supporting the CT device in one apparatus, it is possible to easily construct a radiotherapy apparatus having a constitution like that shown in FIG. 1.

In the radiotherapy apparatus shown in FIG. 1, the therapy radioactive ray source 7 and the collimator 8 are disposed outside the outer wall portion 12, different from the case shown in FIG. 6. Now, a reason for such an arrangement is described. In the tomographic therapy device shown in FIG. 6, the CT device and the radioactive ray irradiating device are integrally rotated. Accordingly, to prevent the clashing of the components of both devices in the high-speed rotating states with the patient, an external object or the like during CT photographing, the components of both devices must be accommodated between the inner and outer wall portions inhibited from being rotated. On the other hand, in the radiotherapy apparatus shown in FIG. 1, only the components of the CT device are rotated at a high speed, and the components of the radioactive ray irradiating device are placed in a stationary state or rotated at a low speed. Accordingly, any protective walls need not be provided as a safety measure for the components of the radioactive irradiating device. However, the components of the CT device are rotated at a high speed with respect to the components of the radioactive ray irradiating device. Thus, to prevent mutual clashing, the components respectively of the CT device and the radioactive ray irradiating device must be separated from each other by the outer wall portion 12. For the inner and outer wall portions 11 and 12, materials and structures should preferably be selected in such a way as to reduce radioactive ray absorption or scattering, and to provide sufficient strength. This way of selection enables effects on the therapy radiation beam 9 to be reduced to a negligible level.

In FIG. 1, a reference numeral 14 denotes an image processing computer for forming a CT image regarding an affected part or the like, creating control information for the apparatus main body 13 based on the formed CT image, and so on; 15 a therapy control computer for controlling each device involved in the execution of radiotherapy based on the control information. An internal network, not shown, is provided to make interconnections between the computers, and between each computer and each device, and information is transferred around by an analog or digital signal. A reference numeral 16 denotes an external network connected to the image processing computer 14, the therapy control computer 15, and an external unit (not-shown). Regarding the connection forms of such networks, in the case of connection between the image processing computer 14 and the therapy control computer 15 should preferably employ a dedicated-line connection form such that real time feedback processing can be guaranteed. In the case of connection with the external system, as real time processing is not important, the network should preferably be constructed by Ethernet of normal 100Base/TX or the like, alternatively a general-purpose LAN having a higher data transfer capability.

Next, the operation of the radiotherapy apparatus is described.

The operator of the radiotherapy apparatus secures the patient 2 to the bed 3 in such a way as to dispose the affected part 2 near the center axis 10. In this state, X-rays are made to radiate from the CT X-ray source 4 while the endless rotating mechanism is rotated. Then, by using the CT X-ray detector 6 to detect the X-rays passed through the patient 1, image pickup data regarding one section of the affected part of the patient 1 is obtained. The image processing computer 14 receives a signal regarding the image pickup data outputted from the CT X-ray detector 6, and forms a CT image of the affected part for each rotation of the endless rotating mechanism. When necessary, such a process is repeated to form a three-dimensional image. Then, based on the formed CT image, the image processing computer 14 creates control information for generating a therapy radiation beam 9 necessary for realizing proper radiotherapy. This created control information is sent as therapy plan information to the therapy control computer 15. In the therapy plan, as in the case of the conventional radiotherapy apparatus, the use of various stationary and dynamic radioactive ray irradiating systems is assumed. For example, it is assumed that one may be selected for use from a fixing irradiation system for fixing the therapy rotating mechanism at a predetermined angle, a rotating irradiation system for rotating the therapy rotating mechanism in a predetermined range of angles, a rotating primary body irradiation system for changing setting for the opening state or the like of the collimator 8 according to the rotation of the therapy rotating mechanism, an intensity-modulation irradiation system for dynamically controlling the collimator 8, and so on. The occurrence of interference between the inner wall portion 11 and the patient 1 or the bed 3 imposes a limitation on the angle setting of the bed 3. In the radiotherapy apparatus of the invention, however, the juxtaposition of the CT device and the radiotherapy apparatus enables the posture of the patient 1, and the position, shape or the like of the bed 3 to be maintained fixed during CT photographing and radiotherapy. Thus, the foregoing angle setting or the like poses no problems.

For the execution of radiotherapy, CT photographing is carried out again with the same posture of the patient 1 and the same position/shape of the bed 3 as those for the CT photographing carried out for creating therapy plan information. The image processing computer 14 compares a CT image used for the creation of the therapy plan information with a CT image obtained immediately before the execution of radiotherapy in a three-dimensional manner by using a collation method called image fusion, and then calculates and outputs the amount of deviation in the position, direction or the like of the affected part. The operator of the radiotherapy apparatus manually or automatically adjusts the position, shape or the like of the bed 3 to correct the outputted amount of deviation, and then the positioning of the patient 1 is completed. As described above, the image processing computer 14 functions as correction amount computing means for comparing the CT image referred to when the therapy plan was made with the CT image obtained immediately before the execution of radiotherapy, and then calculating deviation in the position, direction or the like of the affected part.

In addition, CT photographing may be executed again after the completion of positioning the patient 1, and the CT image for the creation of the therapy plan may be compared with the photographed CT image to verify that the deviation of the affected part 2 has been corrected. In this way, it is possible to further enhance the effectiveness of radiotherapy carried out based on the therapy plan. The CT image obtained immediately before the radiotherapy is compared with the CT image for the creation of the therapy plan, and it is determined that the correction of deviation in the position or direction of the affected part 2 is difficult because of a time or space limitation. In such a case, irrespective of the process before or after the execution of positioning, some changes may added to the therapy plan or a totally new therapy plan may be made to match the state of the affected part 2 immediately before the execution of radiotherapy.

Based on the provided therapy plan, and according to the rotation of the therapy rotating mechanism, the therapy control computer 15 converges the therapy radiation beam 9 radiating from the therapy radioactive ray source 7 by the collimator 8 to match the shape of the affected part 2, and thereby executes radiotherapy. For such an execution of radiotherapy, CT photographing may not be executed. Alternatively, in order to evaluate the effectiveness of the radiotherapy, CT photographing may be executed for recording the state of the currently treated affected part. If CT photographing is not executed, the CT rotating mechanism should preferably be fixed with respect to the therapy rotating mechanism in a range for enabling the therapy radiation beam 9 to be radiate.

If the radiotherapy is executed with CT photographing, the CT device including the CT X-ray source 4 and the CT X-ray detector 6, and the therapy radioactive ray source 7 are continuously operated alternately at short time intervals. Then, by irradiating the affected part 2 alternately with a CT X-ray beam 5 and the therapy radiation beam 9, a CT image can be obtained during the radiotherapy. One to several CT images can be obtained for one rotation of the CT rotating mechanism. A plurality of image pickup data obtained by CT photographing continuously carried out during the radiotherapy are processed by the image processing computer 14. Such processing enables the state of the currently treated affected part 2 to be represented as time and space numerical value information, and the information to be recorded. By obtaining such time and space information regarding the affected part 2 currently subjected to the radiotherapy, it is possible to quantitatively determine positional deviation between a radioactive ray irradiated portion of the affected part targeted by the therapy plan and an actual radioactive ray irradiated portion. As a result, the effectiveness of the executed radiotherapy can be evaluated. Affected part information recording means for recording the time and space information of the affected part during the radiotherapy may be provided in the image processing computer 14, or separately therefrom.

As described above, the CT rotating mechanism and the therapy rotating mechanism are provided so as to be rotated independently of each other. Thus, in the case of executing the radiotherapy with CT photographing, when the therapy radiation beam 9 is made to radiate from the therapy radioactive ray source 7 at an optional angle position, if the therapy radioactive ray source 7 is in a predetermined relative angle range, seen from the center axis 10, with respect to the CT X-ray source 4 and the CT X-ray detector 6, absorption, scattering or the like of the therapy radiation beam 9 by the CT X-ray source or the CT X-ray detector 6 may occur, resulting in interference with the radiotherapy. Therefore, in order to facilitate the smooth execution of radiotherapy, radioactive ray irradiation control means is provided, which functions to detect a relative angle difference between the therapy rotating mechanism and the CT rotating mechanism, and stop the irradiation of radioactive rays from the radioactive ray source 7 in a range, interference occurring in the therapy radiation beam 9 therein. Such radioactive ray irradiation control means can be provided in, for example the therapy control computer 15. The radioactive ray irradiation control means executes control for the irradiation of the therapy radiation beam 9 from the therapy radioactive ray source 7 by transmitting control data through the internal network for interconnecting the therapy control computer 15 and the therapy radioactive ray source 7.

Figure 2:
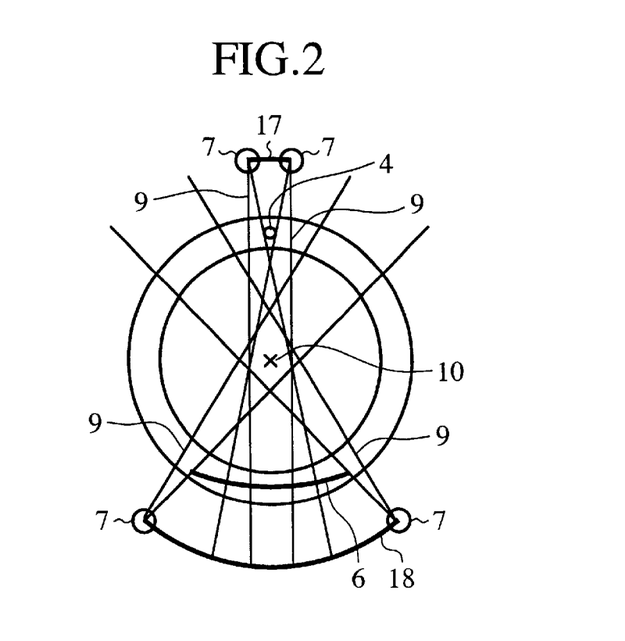
FIG. 2 is a view showing a range of angles for the occurrence of interference in a radiation beam for therapy.

FIG. 2 is a view showing a range of angles for the occurrence of interference in a radiation beam for therapy. In FIG. 2, portions like those in FIG. 1 are denoted by like reference numerals, and thus description thereof will be omitted.

A reference numeral 17 denotes a relative angle range for the therapy radioactive ray source 7 when the radiation beam 9 interferes with the CT X-ray source 4; and 18 a relative angle range for the therapy radioactive ray source 7 when the radiation beam 9 interferes with the CT X-ray detector 6. Accordingly, in the case of the execution of radiotherapy with CT photographing, when it detects that the therapy radioactive ray source 7 is positioned in the relative angle range 17 or 18, the above-noted radioactive ray irradiation control means sends a control signal to the radioactive ray source 7 to stop the irradiation of the therapy radiation beam 9, and secures the smooth execution of the radiotherapy. In the example shown in FIG. 2, the angle range for the occurrence of interference is set only for the state where the therapy radioactive ray source 7 and the CT X-ray source 4, or the CT X-ray detector 6 are located in the same side, seen from the center axis 10. However, there may be a case where the damage or deterioration of the CT X-ray source 4 or the CT X-ray detector 6 caused by the therapy radiation beam 9 is no longer ignored. In such a case, even for the state where the therapy radioactive ray source 7 and the CT X-ray source 4, or the CT-X-ray detector 6 are located in the opposite sides, seen from the center axis 10, it may also be necessary to control the irradiation of the therapy radiation beam 9 by setting an angle range for the occurrence of interference.

As described above, according to the first embodiment, the radiotherapy apparatus comprises the CT rotating mechanism for supporting the CT X-ray source 4 and the CT X-ray detector 6 rotatably around the bed 3, and the therapy rotating mechanism for supporting the radioactive ray source 7 and the collimator 8 rotatably around the bed 3 independently of the CT rotating mechanism. This arrangement enables the CT device composed of the CT X-ray source 4 and the CT X-ray detector 6, and the radioactive ray irradiating device composed of the radioactive ray source 7 and the collimator 8 to be rotated independently of each other and at different speeds. Therefore, the radiotherapy apparatus comprising the CT device and the radioactive ray irradiating device provided side by side is advantageous in that desired and necessary operational characteristics can be secured for the CT device and the radioactive ray irradiating device.

The radiotherapy apparatus also comprises the correction amount computing means for comparing the CT image obtained by photographing carried out by using the CT device and referred to when the therapy plan is made with the CT image obtained by photographing carried out by using the CT device immediately before the radiotherapy, and then computing the amount of deviation in the position, direction or the like of the affected part. This arrangement enables the operator of the radiotherapy apparatus to manually or automatically adjust the position, shape or the like of the bed 3 so as to correct the deviation based on data outputted from the correction amount computing means, thereby positioning the patient as specified in the therapy plan. Therefore, the radiotherapy apparatus is advantageous in that the effectiveness of the radiotherapy executed based on the therapy plan can be enhanced.

In addition, the radiotherapy apparatus comprises the radioactive ray irradiation control means for performing control in such a way as to detect a relative angle difference between the therapy rotating mechanism and the CT rotating mechanism, and stop the irradiation of the radiation beam 9 from the radioactive ray source 7 in the angle range, where interference occurs in the radiation beam 9. This arrangement makes it possible to prevent the absorption, scattering or the like of the therapy radiation beam 9 even when radiotherapy is executed with CT photographing. Therefore, the radiotherapy apparatus is advantageous in that proper radiotherapy can be carried out.

Furthermore, the radiotherapy apparatus comprises the affected part information recording means for recording time and space information regarding the currently treated affected part, obtained by carrying out CT photographing simultaneously with radiotherapy. This arrangement makes it possible to quantitatively determine positional deviation between the radioactive ray irradiated portion of the affected part targeted by the therapy plan and the actual radioactive ray irradiated portion. Therefore, the radiotherapy apparatus is advantageous in that the effectiveness of the executed radiotherapy can be evaluated.

Second Embodiment

Figure 3:
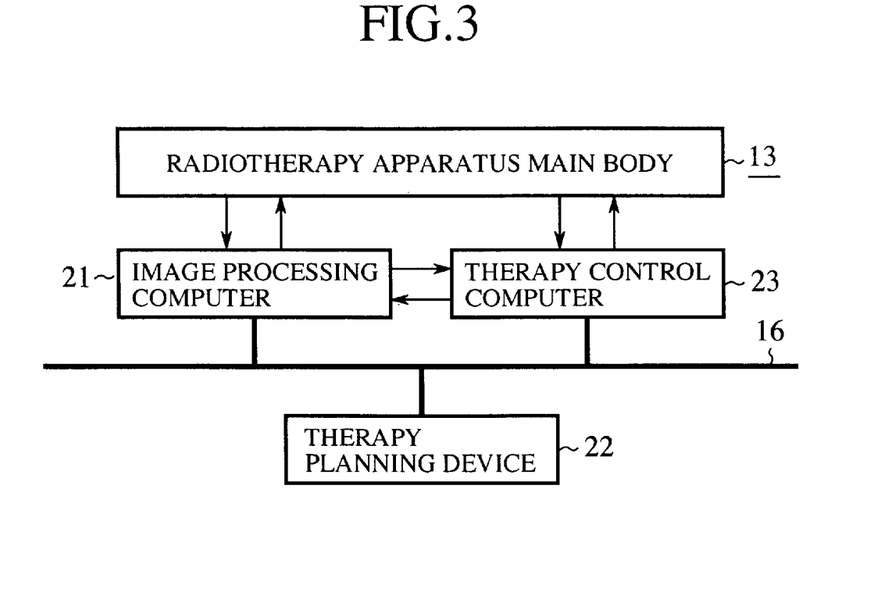
FIG. 3 is a schematic view showing a constitution of a radiotherapy apparatus according to a second embodiment of the invention.

In the foregoing first embodiment, the therapy plan making function is incorporated in the image processing computer 14. The second embodiment described herein is different from the first in that a radiotherapy apparatus is connected to an external therapy planning device having a therapy plan making function through a network. FIG. 3 is a schematic view showing the constitution of the radiotherapy apparatus of the second embodiment. In FIG. 3, components like those shown in FIG. 1 are denoted by like reference numerals, and description thereof will be omitted. A structure inside an apparatus main body denoted by a reference numeral 13 is similar to that shown in FIG. 1. In FIG. 3, a reference numeral 21 denotes an image processing computer (image processing means) for forming a CT image regarding a patient or the like, or performing other operations; 22 a therapy planning device for receiving the entry of CT image data from the image processing computer 21 through an external network 16, and creating control information regarding the apparatus main body 13 by referring to the CT image, or performing other operations; and 23 a therapy control computer (therapy control means) for receiving the entry of the control information from the therapy planning device 22 through the external network 16, and controlling each device involved in the execution of radiotherapy based on the control information.

Now, the operation of the radiotherapy apparatus is described. Operations other than the creation of therapy plan information based on a transmitted CT image, and the transfer of CT image data or data regarding the therapy plan information through the network are similar to those of the first embodiment, and thus description thereof will be omitted.

The image processing computer 21 receives image pickup data regarding the affected part 2 from the CT X-ray detector 6, and forms a CT image regarding the affected part for each rotation of the endless rotating mechanism. When necessary, a three-dimensional image is formed based on a plurality of CT images. Then, the image processing computer 21 sends image data regarding the formed CT image to the therapy planning device 22 through the external network 16. Based on the entered image data, the therapy planning device 22 creates control information, which is used to generate a therapy radiation beam 9 for realizing proper radiotherapy. The therapy planning device 22 then sends the control information created as therapy plan information to the therapy control computer 23 through the external network 16. Based on the received therapy plan information, and according to the rotation of the therapy rotating mechanism, the therapy control computer 23 executes radiotherapy by converging the therapy radiation beam 9 radiating from the therapy radioactive ray source 7, by the collimator 8, to match the shape of the affected part 2.

With regard to a data format or a transfer system for transmitted data such as the CT image, the therapy plan information or the like, for example one may be employed, which is compliant with DICOM examined and presented as a standard by a private committee for the purpose of increasing connectivity between medical image information processing systems. The use of such a system facilitates data transfer between the image processing computer 21 and the therapy planning device 22, and between the therapy control computer 23 and the therapy planning device 22 through the external network 16. As described above with reference to the first embodiment, because of a time or space limitation, there may be a need to add some changes to the therapy plan, or even make a totally new therapy plan according to the state of the affected part 2 immediately before the execution of radiotherapy. In such a case, it is preferred to use the external network having a high-speed data transfer speed.

As apparent from the foregoing, the second embodiment is not only advantageous in a manner similar to that of the first embodiment, but also advantageous in the following respect. Specifically, the radiotherapy apparatus comprises the image processing computer 21 for forming the CT image regarding the affected part or the like, and transmitting the data regarding the CT image through the external network 16, and the therapy control computer 23 for receiving the entry of the therapy plan information through the external network 16, and controlling each device involved in the execution of radiotherapy based on the therapy plan information. Then, the therapy planning device 22 is connected to the external network 16, the therapy planning device 22 being adapted to receive the entry of CT image data and create control information of each device for generating a therapy radiation beam 9 for realizing proper radiotherapy based on the CT image, and data transfer is carried out between the image processing computer 21 and the therapy planning device 22, and between the therapy-control computer 23 and the therapy planning device 22. In this way, an efficient radiotherapy system having a CT device and a radioactive ray irradiating device integrally provided can be constructed by using a commercially available therapy planning device 22 having standard specifications. Therefore, it is possible to reduce development and manufacturing costs for the entire radiotherapy system.

Third Embodiment

The third embodiment of the invention is different from the first and second embodiments in that a radiotherapy apparatus comprises affected part position detecting means for detecting the position of an affected part in real time. This affected part position detecting means can be provided as software inside the image processing computer 14, or separately as a position detector.

Next, the operation of the radiotherapy is described.

Figure 4:
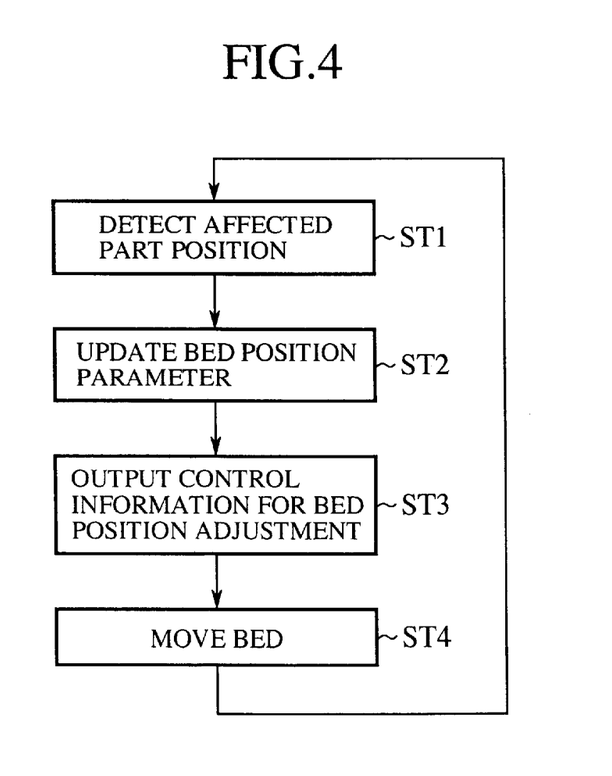
FIG. 4 is a flowchart showing a bed position adjusting process in a radiotherapy apparatus according to a third embodiment of the invention.

FIG. 4 is a flowchart showing a bed position adjustment process carried out in the radiotherapy apparatus of the third embodiment of the invention. By executing radiotherapy with CT photographing, based on each obtained CT image, the affected part position detecting means detects the position of an affected part in real time (step ST1). Then, control means included in the image processing computers 14 and 21, the therapy control computers 15 and 23, or the like updates a parameter for specifying the position of the bed 3 according to deviation between the detected affected part position and the position of the affected part targeted by the therapy plan (step ST2). Then, the therapy control computer 15 or 23 outputs control information for adjusting the position of the bed 3 based on the updated parameter (step ST3). Then, after the entry of the control information, the bed 3 is moved to the set position or transferred to the set form (step ST4). By repeating the process from step ST1 to ST4, the affected part 2 can be held in a predetermined location for the execution of radioactive ray irradiation.

The process from the step ST1 of the detection of the affected part position to the step ST4 of the movement of the bed may take a long time. In other words, in the position correction of the affected part 2, a considerable time delay may occur from the detection of a deviation amount to actual position correction. In such a case, preferably, the moving amount of the affected part before the execution time of the position adjustment of the bed 3 should be predicted based on the time delay, and control information should be created for the position adjustment of the bed according to the predicted moving amount of the affected part. For example, human breathing and the movement of organs following the breathing are cyclical. Accordingly, the movement of the affected part may be approximated by a proper cycle curve along the time axis of a sine function or the like, based on the moving history of the affected part following the breathing. In this way, the position of the affected part at the execution time of the position adjustment of the bed 3 can be predicted based on the position of the affected part detected by the affected part position detecting means at given time. Therefore, by creating control information based on such position prediction made by considering the cyclic movement of the affected part in step ST3, it is possible to carry out radiotherapy with higher accuracy.

As described above, according to the third embodiment, the radiotherapy apparatus comprises the affected part position detecting means for detecting the position of the affected part in real time. This arrangement enables the affected part 2 to be held in a predetermined location to be irradiated with radioactive rays by adjusting the position of the bed 3 each time according to the position of the affected part detected in real time. Therefore, the radiotherapy apparatus is advantageous in that the effectiveness of radiotherapy can be enhanced. Moreover, the radiotherapy apparatus is advantageous in that it is possible to carry out radiotherapy with higher accuracy by creating control information regarding a position adjustment based on the position of the affected part detected in real time, and the amount of movement of the affected part -predicted to be made due to breathing or the like before the execution time of the position adjustment of the bed 3.

Fourth Embodiment

The fourth embodiment of the invention is different from the first and second embodiments in that a radiotherapy apparatus comprises affected part shape detecting means for detecting the shape of an affected part in real time. This affected part shape detecting means can be provided as software in the image processing computer 14 or 21, or separately as a shape detector.

Next, the description of the radiotherapy apparatus is described.

Figure 5:
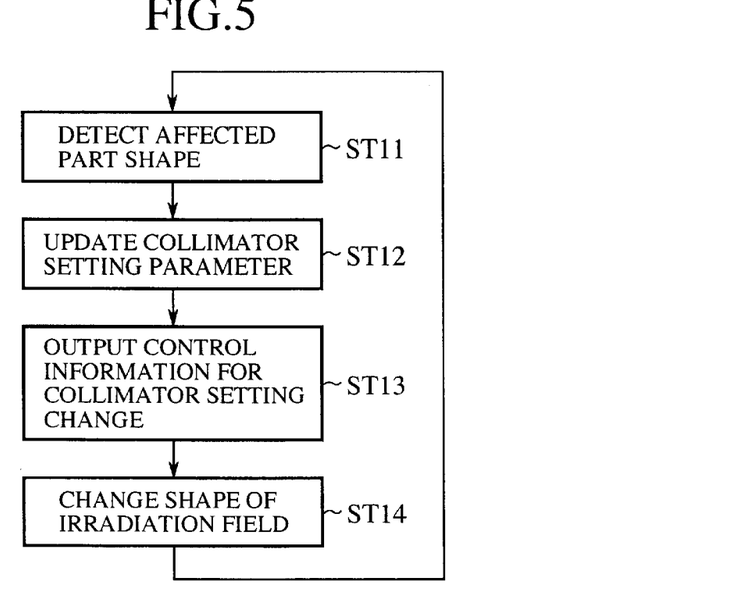
FIG. 5 is a flowchart showing a collimator adjusting process in a radiotherapy apparatus according to a fourth embodiment of the invention.

FIG. 5 is a flowchart showing the process of collimator adjustment carried out in the radiotherapy apparatus of the fourth embodiment of the invention. Radiotherapy is executed with CT photographing and, based on each CT image thereby obtained, the affected part shape detecting means detects the shape of the affected part in real time (step ST11). Then, control means included in the image processing computers 14 and 21, the therapy control computers 15 and 23, or the like updates a parameter for setting the opening state or the like of the collimator 8 in order to obtain a predetermined field of irradiation according to deviation between the detected affected part shape and the shape of the affected part targeted by the therapy plan (step ST12). Then, the therapy control computer 15 or 23 outputs control information for changing the setting of the collimator 8 based on the updated parameter (step ST13). Then, after the entry of the control information, the collimator 8 changes setting regarding an opening state or the like to obtain a predetermined field of irradiation (step ST14). By repeating the process from step ST11 to ST14, a proper field of irradiation can be obtained in accordance with the shape change of the affected part 2.

The process from the step ST11 of the detection of the affected part shape to the step ST14 of the setting change of the collimator 8 may take a long time. In other words, in the shape correction of the field of irradiation, a considerable time delay may occur from the detection of affected part shape deviation to actual shape correction of the field of irradiation. In such a case, preferably, the degree of deformation of the affected part before the execution time of the setting change of the collimator 8 should be predicted based on the time delay, and control information should be created for the setting change of the collimator according to the predicted degree of deformation of the affected part. For example, human breathing and the deformation of organs following the breathing are cyclical. Accordingly, the deformation of the affected part may be approximated by a proper cycle curve along the time axis of a sine function or the like, based on the deformation history of the affected part following the breathing. In this way, the shape of the affected part at the execution time of the setting change of the collimator 8 can be predicted based on the shape of the affected part detected by the affected part shape detecting means at given time. Therefore, by creating control information based on such shape prediction made by considering the cyclic deformation of the affected part in step ST13, it is possible to carry out radiotherapy with higher accuracy.

As described above, according to the fourth embodiment, the radiotherapy apparatus comprises the affected part shape detecting means for detecting the shape of the affected part in real time. This arrangement enables a proper field of irradiation to be formed to match the shape change of the affected part 2 by changing setting of the collimator 8 each time according to the shape of the affected part detected in real time. Therefore, the radiotherapy apparatus is advantageous in that the effectiveness of radiotherapy can be enhanced. Moreover, the radiotherapy apparatus is advantageous in that it is possible to carry out radiotherapy with higher accuracy by creating control information regarding a setting change based on the shape of the affected part detected in real time, and the degree of deformation of the affected part predicted to be made due to breathing or the like before the execution time of the setting change of the collimator 8.

As described above, according to the present invention, the radiotherapy apparatus comprises: the bed, the position thereof being adjustable; the CT X-ray source; the CT X-ray detector; the CT rotating mechanism for supporting the CT X-ray source and the CT X-ray detector rotatably around the bed; the radioactive source for irradiating radioactive rays for therapy; the collimator provided for converging the beam shape of the therapy radioactive rays radiating from the radioactive ray source; and the therapy rotating mechanism for supporting the radioactive ray source and the collimator rotatably around the bed independently of the CT rotating mechanism. This arrangement enables the CT device composed of the CT X-ray source and the CT X-ray detector, and the radioactive ray irradiating device composed of the radioactive ray source and the collimator to be rotated independently of each other and at different speeds. Therefore, the radiotherapy apparatus comprising the CT device and the radioactive ray irradiating device provided side by side is advantageous in that desired and necessary operational characteristics can be secured for the CT device and the radioactive ray irradiating device.

According to the invention, the radiotherapy apparatus comprises: the correction amount computing means for comparing the CT image obtained by photographing carried out by using the CT device and referred to when the therapy plan is made with the CT image obtained by photographing carried out by using the CT device immediately before the radiotherapy, and then computing the amount of deviation in the position, direction or the like of the affected part. This arrangement enables the operator of the radiotherapy apparatus to manually or automatically adjust the position, shape or the like of the bed so as to correct the deviation based on data outputted from the correction amount computing means, thereby positioning the patient as specified in the therapy plan. Therefore, the radiotherapy apparatus is advantageous in that the effectiveness of the radiotherapy executed based on the therapy plan can be enhanced.

According to the invention, the radiotherapy apparatus comprises: the radioactive ray irradiation control means for performing control in such a way as to detect a relative angle difference between the therapy rotating mechanism and the CT rotating mechanism, and stop the irradiation of radioactive rays from the radioactive ray source in the angle range, where interference occurs in the radioactive rays for therapy. This arrangement makes it possible to prevent the absorption, scattering or the like of the therapy radioactive rays even when radiotherapy is executed with CT photographing. Therefore, the radiotherapy apparatus is advantageous in that proper radiotherapy can be carried out.

According to the invention, the radiotherapy apparatus comprises; the affected part information recording means for recording time and space information regarding the currently treated affected part, obtained by carrying out CT photographing simultaneously with radiotherapy. This arrangement makes it possible to quantitatively determine positional deviation between the radioactive ray irradiated portion of the affected part targeted by the therapy plan and the actual radioactive ray irradiated portion. Therefore, the radiotherapy apparatus is advantageous in that the effectiveness of the executed radiotherapy can be evaluated.

According to the invention, the radiotherapy apparatus comprises: the image processing means for forming the CT image regarding the affected part or the like, and transmitting the data regarding the CT image through the network; and the therapy control means for receiving the entry of the therapy plan information through the network, and controlling each device involved in the execution of radiotherapy based on the therapy plan information. Then, the therapy planning device is connected to the network, the therapy planning device being adapted to receive the entry of CT image data and create control information of each device for generating therapy radioactive rays for executing shape setting regarding therapy radioactive rays for realizing proper radiotherapy based on the CT image, and data transfer is carried out between the image processing means and the therapy planning device, and between the therapy control means and the therapy planning device. In this way, an efficient radiotherapy system having a CT device and a radioactive ray irradiating device integrally provided can be constructed by using a commercially available therapy planning device having standard specifications. Therefore, it is possible to reduce development and manufacturing costs for the entire radiotherapy system.

According to the invention, the radiotherapy apparatus comprises: the affected part position detecting means for detecting the position of the affected part in real time. This arrangement enables the affected part to be held in a predetermined location to be irradiated with radioactive rays by adjusting the position of the bed each time according to the position of the affected part detected in real time. Therefore, the radiotherapy apparatus is advantageous in that the effectiveness of radiotherapy can be enhanced. Moreover, the radiotherapy apparatus is advantageous in that it is possible to carry out radiotherapy with higher accuracy by creating control information regarding a position adjustment based on the position of the affected part detected in real time, and the amount of movement of the affected part predicted to be made due to breathing or the like before the execution time of the position adjustment of the bed.

According to the invention, the radiotherapy apparatus comprises: the affected part shape detecting means for detecting the shape of the affected part in real time. This arrangement enables a proper field of irradiation to be formed to match the shape change of the affected part by changing setting of the collimator each time according to the shape of the affected part detected in real time. Therefore, the radiotherapy apparatus is advantageous in that the effectiveness of radiotherapy can be enhanced. Moreover, the radiotherapy apparatus is advantageous in that it is possible to carry out radiotherapy with higher accuracy by creating control information regarding a setting change based on the shape of the affected part detected in real time, and degree of deformation of the affected part predicted to be made due to breathing or the like before the execution time of the setting change of the collimator.

The present invention is not limited to the above-described embodiments, and variations and modifications may be made without departing from the scope of the present invention.

What is claimed is:

1. A radiotherapy apparatus comprising:
   a bed, a position thereof being adjustable;
   an X-ray source for CT;
   an X-ray detector for CT;
   a CT rotating mechanism for supporting the CT X-ray source and the CT X-ray detector rotatably around the bed;
   a radioactive ray source for irradiating radioactive rays for therapy;
   a collimator provided for converging a shape of a therapy radiation beam radiating from the radioactive ray source; and
   a therapy rotating mechanism for supporting the radioactive ray source and the collimator rotatably around the bed independently of the CT rotating mechanism.

2. A radiotherapy apparatus according to claim 1, further comprising: correction amount computing means for computing deviation in a position or a direction of an affected part by comparing a CT image obtained by photographing carried out by using a CT device composed of a CT X-ray source and a CT X-ray detector, and referred to when a therapy plan is made, with a CT image obtained by photographing carried out by using the CT device immediately before radiotherapy.

3. A radiotherapy apparatus according to claim 1, further comprising: radioactive ray irradiation control means for performing control to detect a relative angle difference between the therapy rotating mechanism and the CT rotating mechanism, and to stop irradiation of radioactive rays from the radioactive ray source in a range of angles, interference occurring in therapy radioactive rays therein.

4. A radiotherapy apparatus according to claim 3, wherein affected part information recording means is provided for recording time and space information regarding an affected part currently subjected to radiotherapy, obtained by executing CT photographing simultaneously with the radiotherapy.

5. A radiotherapy apparatus according to claim 1, further comprising: image processing means for forming a CT image regarding an affected part or the like, and transmitting data of the CT image through a network; and therapy control means for receiving an entry of therapy plan information through the network, and controlling each device involved in execution of radiotherapy based on the therapy plan information.

6. A radiotherapy apparatus according to claim 1, further comprising: affected part position detecting means for detecting an affected part position in real time.

7. A radiotherapy apparatus according to claim 1, further comprising: affected part shape detecting means for detecting an affected part shape in real time.

* * * * *